(12) United States Patent
Fiandaca et al.

(10) Patent No.: US 10,670,617 B2
(45) Date of Patent: Jun. 2, 2020

(54) METHODS OF ASSESSING FUTURE MEMORY LOSS BY MEASURING POLYUNSATURATED FATTY ACIDS

(71) Applicant: Georgetown University, Washington, DC (US)

(72) Inventors: Massimo S. Fiandaca, Irvine, CA (US); Howard J. Federoff, Irvine, CA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 15/580,984

(22) PCT Filed: Jun. 8, 2016

(86) PCT No.: PCT/US2016/036397
§ 371 (c)(1),
(2) Date: Dec. 8, 2017

(87) PCT Pub. No.: WO2016/200903
PCT Pub. Date: Dec. 15, 2016

(65) Prior Publication Data
US 2018/0196073 A1    Jul. 12, 2018

Related U.S. Application Data

(60) Provisional application No. 62/172,636, filed on Jun. 8, 2015, provisional application No. 62/194,223, filed on Jul. 18, 2015.

(51) Int. Cl.
| | | |
|---|---|---|
| *G01N 33/92* | (2006.01) | |
| *A61K 31/00* | (2006.01) | |
| *A61K 31/20* | (2006.01) | |
| *A61K 38/00* | (2006.01) | |
| *A61K 31/202* | (2006.01) | |
| *G01N 33/52* | (2006.01) | |
| *G01N 33/48* | (2006.01) | |
| *A61K 31/201* | (2006.01) | |

(52) U.S. Cl.
CPC ............. *G01N 33/92* (2013.01); *A61K 31/20* (2013.01); *A61K 31/201* (2013.01); *A61K 31/202* (2013.01); *G01N 33/48* (2013.01); *G01N 33/52* (2013.01); *G01N 2800/2814* (2013.01); *G01N 2800/2871* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2003/0211622 A1    11/2003    Robert, II

FOREIGN PATENT DOCUMENTS

| WO | 2007/098020 A2 | 8/2007 |
|---|---|---|
| WO | 2015/027116 A1 | 2/2015 |

OTHER PUBLICATIONS

International Search Report issued in corresponding International Patent Application No. PCT/US2016/036397 dated Sep. 16, 2016.
Bazinet et al., Polyunsaturated fatty acids and their metabolites in brain function and disease, Nature ReviewsNeuroscience, 2014, 15:771-785.
Hamilton et al., Brain uptake and utilization of fatty acids, lipids and lipoproteins: application to neurological disorders, J. Mol. Neurosci., 2007, 33:2-11.

*Primary Examiner* — Olga N Chernyshev
(74) *Attorney, Agent, or Firm* — Haug Partners LLP

(57) ABSTRACT

The present invention relates to methods of determining if a subject has an increased risk of suffering from memory impairment. The methods comprise determining the influx of polyunsaturated fatty acids (PUFAs) into the brain from plasma in a test subject and comparing this measured influx to a normal standard influx. An increase in influx of PUFAs from the plasma into the brain is indicative that the subject has an increased risk of suffering from memory impairment compared to a normal individual.

14 Claims, 2 Drawing Sheets

METHODS OF ASSESSING FUTURE MEMORY LOSS BY MEASURING POLYUNSATURATED FATTY ACIDS

STATEMENT REGARDING FEDERALLY SPONSORED RESEARCH OR DEVELOPMENT

This invention was made with government support under grant number R04 AG030753 awarded by the National Institutes of Health and under contract number W81XWH-09-1-0107 awarded by the Department of Defense. The government has certain rights in the invention.

BACKGROUND OF THE INVENTION

Field of the Invention

The present invention relates to methods of determining if a subject has an increased risk of suffering from memory impairment. The methods comprise determining the influx of polyunsaturated fatty acids (PUFAs) into the brain from plasma in a test subject and comparing this measured influx to a normal standard influx. An increase in influx of PUFAs from the plasma into the brain is indicative that the subject has an increased risk of suffering from memory impairment compared to a normal individual.

Background of the Invention

Alzheimer's disease (AD) is a neurodegenerative disorder characterized by a progressive dementia that insidiously and inexorably robs older adults of their memory and other cognitive abilities. The prevalence of AD is expected to double every 20 years from 35.6 million individuals worldwide in 2010 to 115 million affected individuals by 2050. There is no cure and current therapies are unable to slow the disease progression.

Early detection of the at-risk population (preclinical), or those in the initial symptomatic stages (prodromal) of AD, may present opportunities for more successful therapeutic intervention, or even disease prevention by interdicting the neuropathological cascade that is characterized by the deposition of extracellular β-amyloid (Aβ) and accumulation of intracellular fibrils of microtubular hyperphosphorylated tau protein within the brain. Biomarkers for early disease, including cerebrospinal fluid (CSF) tau and Aβ levels, structural and functional magnetic resonance imaging (MRI), and the recent use of brain amyloid imaging, are of limited use for widespread screening since they provide diagnostic options that are either invasive, i.e., require lumbar puncture, time-consuming, i.e., several hours in a scanner for most comprehensive imaging protocols, or expensive. No current blood-based biomarkers can detect incipient dementia with the required sensitivity and specificity at a preclinical stage. Continued interest in blood-based biomarkers remains because these specimens are obtained using rapid, minimally invasive methods. With recent technological advances in 'omics' and systems level approaches, the comprehensive bioinformatic analyses of prognostic biomarkers may yield new insights into the underlying mechanisms and pathobiological networks of AD and possibly herald the development of new therapeutic strategies.

The preclinical interval resulting in mild cognitive impairment (MCI) or AD is known to be variable, multifactorial, and extends up to 7-10 years prior to the emergence of clinical signs. In the absence of valid and reliable biomarkers, multimodal neurocognitive testing remains the most accurate, standardized, and widely used pre-mortem screening method to determine clinical MCI or AD. The utility of strict cognitive assessment for preclinical states of MCI or AD is limited, however, as this approach is time-consuming and expected to be present almost all individuals as normal, as it quantitatively delineates specific brain properties, such as language, thought, and behavior, which is typically not affected in individual in the preclinical state. Thus, what is needed is a diagnostic method that is quick, effective, less invasive and accurate in determining future onset of MCI and/or AD.

SUMMARY OF THE INVENTION

The present invention relates to methods of determining if a subject has an increased risk of suffering from memory impairment. The methods comprise determining the influx of polyunsaturated fatty acids (PUFAs) into the brain from plasma in a test subject and comparing this measured influx to a normal standard influx. An increase in influx of PUFAs from the plasma into the brain is indicative that the subject has an increased risk of suffering from memory impairment compared to a normal individual.

BRIEF DESCRIPTION OF THE DRAWINGS

FIG. 1 depicts a schematic representation of potential alterations within brain and peripheral blood responsible for reduced plasma phospholipid levels. 1A shows a theoretical qualitative dot plot of differential changes occurring in cognitively normal control (NC), cognitively normal Converter$_{pre}$ (Cpre) subjects, and those with amnestic mild cognitive impairment or Alzheimer's disease (aMCI/AD). Note that all four processes are at the zero relative level in the NC subjects. Going from left to right, the first dot is the levels of PUFA influx into the brain; the second dot is levels of plasma PUFAs, the third dot is level of active neuroinflammation and the last dot on the right is the degree of brain injury. The Cpre subjects show significant transport of polyunsaturated fatty acid (PUFA) into the brain, likely to replenish lost substrate from inflammation, oxidative stress or other brain injury or metabolic abnormality. The increase in PUFA flux into the brain is an attempt to compensate for ongoing injury and results in a marked reduction in the plasma levels of molecules carrying those lipid species. 1B. shows qualitative depiction of plasma phospholipid biomarker results previously quantified and specified (Mapstone et al., 2014, Fiandaca, et al., Alzheimer's & Dementia 10 (2014) S196-S212). Dark horizontal line within boxes represents proposed mean levels of metabolites for the group.

FIG. 2A depicts the results of the ROC analysis of baseline PADI on phenoconversion to MCI/AD (AUC=0.93); FIG. 2B depicts the survival analysis of baseline PADI on accumulative MCI/AD cases over 5 years adjusting for age, years of education, APOE4 carrier, global cognition, depression, and memory complaints.

DETAILED DESCRIPTION OF THE INVENTION

The present invention relates to methods of determining if a subject has an increased risk of suffering from memory impairment. The methods comprise determining the influx of polyunsaturated fatty acids (PUFAs) into the brain from plasma in a test subject and comparing this measured influx to a normal standard influx. An increase in influx of PUFAs from the plasma into the brain is indicative that the subject has an increased risk of suffering from memory impairment compared to a normal individual.

As used herein, the term subject or "test subject" indicates a mammal, in particular a human or non-human primate. The test subject may or may not be in need of an assessment of a predisposition to memory impairment. For example, the test subject may have a condition or may have been exposed to injuries or conditions that are associated with memory impairment prior to applying the methods of the present invention. In another embodiment, the test subject has not been identified as a subject that may have a condition or may have been exposed to injuries or conditions that are associated with memory impairment prior to applying the methods of the present invention.

As used herein, the phrase "memory impairment" means a measureable or perceivable decline or decrease in the subject's ability to recall past events. As used herein, the term "past events" includes both recent (new) events (short-term memory) or events further back in time (long-term memory). In one embodiment, the methods are used to assess an increased risk for short-term memory impairment. In another embodiment, the methods are used to assess an increased risk for long-term memory impairment. The measureable or perceivable decline in the subject's ability to recall past events may be assessed clinically by a health care provider, such as a physician, physician's assistant, nurse, nurse practitioner, psychologist, psychiatrist, hospice provider, or any other provider that can assess a subject's memory. The measureable or perceivable decline in the subject's ability to recall past events may be assessed in a less formal, non-clinical manner, including but not limited to the subject himself or herself, acquaintances of the subject, employers of the subject and the like. The invention is not limited to a specific manner in which the subject's ability to recall a past event is assessed. In fact, the methods of the invention can be implemented without the need to assess a subject's ability to recall past events. Of course, the methods of the present invention may also include assessing the subject's ability to assess past events one or more times, both before determining the subject's influx levels and after determining the subject's influx levels at least one time.

In one embodiment, the methods may also comprise assessing the individual's Preclinical Alzheimer's Disease Index (PADI). As used herein, PADI is an assessment of an individual's likelihood of developing memory impairment based on a novel, synthetic scoring valuation comprising a memory component and an attention component. In one embodiment, the PADI of the individual is assessed prior to determining the subject's PUFA profile and the PUFA profile is then used to further stratify subjects that are considered at risk of suffering from memory impairment based on the PADI. In another embodiment, the PADI of the individual is assessed after determining the subject's PUFA profile and the PADI is then used to further stratify subjects that are considered at risk of suffering from memory impairment based on the PUFA profile. In yet another embodiment, the PADI profile and the PUFA profile are assessed in conjunction with one another such that the combined composite profile is determined prior to any initial patient population stratification.

In one embodiment, the PADI is calculated as a simple ratio between attention performance evaluations and memory performance evaluations. In one embodiment, the PADI is calculated as a weighted ratio between attention performance evaluations and memory performance evaluations. In specific embodiments, the attention component is weighted less than the memory component in calculating the PADI, i.e., the value of the attention is component less than 1:1, i.e., between about 0.001 and about 0.499. In more specific embodiments, the attention component is weighted between about 0.499 about 0.200, between about 0.490 and about 0.300 and between about 0.485 and about 0.400. Conversely, in some embodiments, the memory component is weighted more than the attention component in calculating the PADI, i.e., the value of the attention component is more than 1:1, i.e., between about 0.501 and about 0.999. For example, in more specific embodiments, the memory component is weighted between about 0.501 and 0.800, between about 0.510 and about 0.700 and between about 0.515 and about 0.600. Of course, the signs of relative weights in determining the ratios could be reversed for each component, e.g., the weight of the attention component could be between −0.001 and −0.500 and the weight of the memory component could be between about −0.0500 and −0.999 such that the "higher" PADI score indicates that the subject has a higher risk of suffering from memory impairment.

As used herein, the phrase "PUFA profile" (or "metabolite profile") means the combination of a subject's PUFAs found in the peripheral blood or portions thereof, such as but not limited to plasma or serum. The PUFA profile is a collection of measurements, such as but not limited to a quantity or concentration, for individual metabolites taken from a test sample of the subject. Examples of test samples or sources of components for the PUFA profile include, but are not limited to, biological fluids, which can be tested by the methods of the present invention described herein, and include but are not limited to whole blood, such as but not limited to peripheral blood, serum, plasma, cerebrospinal fluid, urine, amniotic fluid, lymph fluids, and various external secretions of the respiratory, intestinal and genitourinary tracts, tears, saliva, milk, white blood cells, myelomas and the like. Test samples to be assayed also include but are not limited to tissue specimens including normal and abnormal tissue.

In specific embodiments, the subject's PUFA profile is combined with the subject's PADI to provide a composite score for assessing the risk that the subject will suffer from future memory impairment. Accordingly, select embodiments of the methods of the present invention comprise obtaining a PUFA profile, obtaining a PADI and combining each of the profiles to obtain a composite profile having a performance component and a biological component.

In one embodiment, the composite profile is calculated as a simple ratio between the PADI and the PUFA profile. In one embodiment, the composite profile is calculated as a weighted ratio between the PADI and the PUFA profile. In specific embodiments, the PADI component is weighted less than the PUFA component in calculating the composite profile, i.e., the value of the PADI component is less than 1:1, i.e., between about 0.001 and about 0.499. In more specific embodiments, the PADI component is weighted between about 0.499 about 0.200, between about 0.490 and about 0.300 and between about 0.485 and about 0.400. In additional embodiments, the PADI component is weighted more than the PUFA component in calculating the composite profile, i.e., the value of the PADI component is more than 1:1, i.e., between about 0.501 and about 0.999. For example, in more specific embodiments, the PADI component is weighted between about 0.501 and 0.800, between about 0.510 and about 0.700 and between about 0.515 and about 0.600. Conversely, in some embodiments, the PUFA component is weighted more than the PADI component in calculating the composite, i.e., the value of the PADI component is more than 1:1, i.e., between about 0.501 and about 0.999. For example, in more specific embodiments, the PUFA component is weighted between about 0.501 and 0.800, between about 0.510 and about 0.700 and between about 0.515 and about 0.600. In additional embodiments, the PUFA component is weighted less than the PADI component in calculating the composite profile, i.e., the value of the PUFA component is less than 1:1, i.e., between about 0.001 and about 0.499. In more specific embodiments, the PUFA component is weighted between about 0.499 about 0.200, between about 0.490 and about 0.300 and between about 0.485 and about 0.400. Of course, the signs of relative weights in determining the composite could be reversed for each component, e.g., the weight of the PADI component could be between −0.001 and −0.500 and the weight of the PUFA component could be between about −0.0500 and −0.999 such that the "higher" composite profile indicates that the subject has a higher risk of suffering from memory impairment.

In one embodiment, the decline or decrease in the ability to recall past events is relative to each individual's ability to recall past events prior to the diagnosed decrease or decline in the ability to recall past events. In another embodiment, the decline or decrease in the ability to recall past events is relative to a population's (general, specific or stratified) ability to recall past events prior to the diagnosed decrease or decline in the ability to recall past events.

As used herein, the term means "increased risk" is used to mean that the test subject has an increased chance of developing or acquiring memory impairment compared to a normal individual. The increased risk may be relative or absolute and may be expressed qualitatively or quantitatively. For example, an increased risk may be expressed as simply determining the subject's PUFA flux levels and placing the patient in an "increased risk" category, based upon previous PUFA flux population studies. Alternatively, a numerical expression of the subject's increased risk may be determined based upon the measured PUFA flux levels. As used herein, examples of other expressions of an increased risk include but are not limited to, odds, probability, odds ratio, p-values, attributable risk, relative frequency, positive predictive value, negative predictive value, and relative risk.

While the brain has the capacity to generate all of the lipid species it requires for normal function, in addition to most saturated and mono-unsaturated fatty acids, the substrates required for such independent maintenance of brain lipid homeostasis, especially sources of energy and PUFAs, are delivered via the bloodstream. In normal brain processing, lipid precursor components are recycled and have relatively long half-lives, especially certain fatty acid components of phospholipids (Edmond, 2001). Some PUFAs, such as docosahaxaenoic acid (DHA; 22:6 n-3) and arachidonic acid (AA; 20:4 n-6) provide structural functionality as phospholipid components in bilayer membranes and, once released, either directly or through byproducts, participate in signal transduction processes with both positive and negative consequences within cells. In cases where brain membrane lipids undergo catabolism, e.g., cases of oxidative stress, or neuroinflammation, the downstream intermediates often are not recycled, thereby increasing demand for lipid precursors from the bloodstream. Such precursors exist in plasma as unesterified fatty acids (FAs) 22 carbons) bound to albumin, or as esterified FA components (>22 carbons) incorporated into circulating phospholipid species preferentially transported within lipoproteins. Triacylglycerols, diacylglycerophospholipids and lysophosphoglycerophospholipids represent major circulating esterified forms. Certain lysophosphatidylcholine species appear to be more efficiently transported into the brain from plasma compared to triacylglycerol or unesterified fatty acids (Lagarde et al., 2001). Esterified FAs are typically converted to unesterified forms by lipases within the lipoproteins or within the blood, prior to their passage (or flux) into the brain. Flux of unesterified FAs into the brain, across the blood-brain barrier (BBB), occurs via simple diffusion and possibly via facilitated transport. All unesterified FAs entering the brain are immediately esterified by acetyl-CoA-synthase, preventing their diffusion back to blood and preparing them for incorporation into lipid synthetic pathways or for β-oxidation. Activation of phospholipases, e.g., PLA2, with increased oxidative stress, is implicated in diminishing PUFAs from PCs and other lipid species within cellular membranes. Esterified FAs are converted to unesterified forms by lipases within the lipoproteins or within the blood, prior to their passage (or flux) into the brain. Flux of unesterified FAs into the brain, across the blood-brain barrier (BBB), occurs via simple diffusion and possibly via facilitated transport. All unesterified FAs entering the brain are immediately esterified by acetyl-CoA-synthase, preventing their diffusion back to blood and preparing them for incorporation into lipid synthetic pathways or for β-oxidation. Activation of phospholipases, e.g., $PLA_2$, with increased oxidative stress, is implicated in diminishing PUFAs from PCs and other lipid species within cellular membranes.

Thus measuring plasma fatty acids, in particular, measuring their flux into the central nervous system, provides a key indicator of ongoing abnormal lipid metabolism in the brain, which, in turn, can signify an active process of brain injury and/or pending development of memory loss. In one embodiment, the fatty acids are polyunsaturated fatty acids (PUFAs). In a more specific embodiment, the PUFAs used in the methods of the present invention are omega-3 fatty acids and/or omega-6 fatty acids. In another specific embodiment, the PUFAs for which influx is measured are essential fatty acids.

Omega-3 PUFAs include but are not limited to Hexadecatrienoic acid (HTA), Alpha-linolenic acid (ALA), Stearidonic acid (SDA), Eicosatrienoic acid (ETE), Eicosatetraenoic acid (ETA), Eicosapentaenoic acid (EPA), Heneicosapentaenoic acid (HPA), Docosapentaenoic acid (DPA) Docosahexaenoic acid (DHA), Tetracosapentaenoic acid and Tetracosahexaenoic acid (Nisinic acid). In certain embodiment, the influx of any one or more of the omega-3 fatty acids listed herein can be used in any of the methods of the present invention.

Omega-6 PUFAs include but are not limited to Linoleic acid (LA), Gamma-linolenic acid (GLA), Eicosadienoic acid, Dihomo-gamma-linolenic acid (DGLA), Arachidonic acid (AA), Docosadienoic acid, Adrenic acid, Docosapentaenoic acid (Osbond acid), Tetracosatetraenoic acid and Tetracosapentaenoic acid. In certain embodiment, the influx of any one or more of the omega-6 fatty acids listed herein can be used in any of the methods of the present invention.

In one embodiment, the PUFAs used in the methods of the present invention are the essential fatty acids alpha linolenic acid (ALA) or linoleic acid (LA). In another embodiment, both ALA and LA are used in the methods of the present invention.

In another embodiment, the PUFAs used in the methods of the present invention are EPA, DHA and/or AA. In another embodiment, EPA and DHA are used in the methods of the present invention. In another embodiment, AA and DHA are used in the methods of the present invention. In another embodiment, EPA and AA are used in the methods of the present invention. In another embodiment, AA, EPA and DHA are used in the methods of the present invention.

To measure influx of the PUFAs used in the methods of the present invention, the PUFAs can be labeled and then administered to the subject. Current methods and equipment can then be used to trace and monitor the movement of the labeled PUFAs from the circulation into the brain ("influx") of the subject. As used herein, the term "influx" refers to the movement of a molecule, such as a labeled PUFA, into the brain and across the blood brain barrier of a subject, such that the labeled PUFA would no longer be considered as being in the general circulation. Routes of administration of the labeled PUFAs are well known and include oral, nasal, intravenous injection, intramuscular injection, intraperitoneal injection and the like. The methods of the present invention are not limited to the routes of administration of the labeled PUFA.

In select embodiments, the PUFAs used in the methods of the present invention are labeled using a radioactive isotope. For example, the Carbon-11 (11C) isotope can be used to label the PUFAs to be measured, by incorporating 11C into any of the PUFA carbon atoms. Ideally, the carboxyl carbon ($\Delta$ 1) or adjacent carbon ($\Delta$ 2) would be tagged and allow that specific molecule to be monitored via positron emission tomography (PET) scanning as it migrates from blood to brain. The chemical tagging of PUFAs with 11C is a known method for physiological monitoring and along with PET scanning to allow determination of flux of 11C-tagged substances into the brain.

Once administered the labeled PUFAs can be monitored using equipment designed to detect and trace the label. For example, if the PUFAs are labeled using Carbon-11, which decay via positron emission, the influx of the labeled PUFAs can be measured using well-known positron emission tomography (PET) techniques. In another example, if the PUFAs are labeled with a fluorescent dye, e.g., BODIPY™ (4,4-difluoro-3a,4adiaza-s-indacene), the influx of the labeled PUFAs can be measured using in vivo fluorescent microscopy.

The correlation between a subject's measured PUFA flux value and the likelihood of suffering from memory impairment may be measured by an odds ratio (OR) and by the relative risk (RR). If $P(R^+)$ is the probability of developing memory impairment for individuals with the determined influx levels (R) and $P(R^-)$ is the probability of developing memory impairment for individuals having normal influx levels, then the relative risk is the ratio of the two probabilities: $RR=P(R^+)/P(R^-)$.

In case-control studies, however, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of measured influx levels in cases studies and $F^-$ is the frequency of measured influx levels in controls. $F^+$ and $F^-$ can be calculated using the measured d influx level frequencies of the study.

The attributable risk (AR) can also be used to express an increased risk. The AR describes the proportion of individuals in a population exhibiting memory impairment due to a certain minimum or maximum influx level. The public health relevance of the AR measurement lies in estimating the proportion of cases of memory impairment in the population that could be prevented if the influx levels were not abnormal. AR may be determined as follows: $AR=P_E(RR-1)/(P_E(RR-1)+1)$, where AR is the risk attributable to a minimum (or maximum) measured influx, and $P_E$ is the frequency of certain influx level within the population at large. RR is the relative risk, which can be approximated with the odds ratio when the influx levels under study have a relatively low incidence in the general population.

In one embodiment, the increased risk of a patient can be determined from p-values that are derived from association studies. Specifically, associations with specific PUFA flux levels can be performed using regression analysis by regressing the PUFA flux levels with memory impairment. In addition, the regression may or may not be corrected or adjusted for one or more factors. The factors for which the analyses may be adjusted include, but are not limited to age, sex, weight, ethnicity, geographic location, fasting state, state of pregnancy or post-pregnancy, menstrual cycle, general health of the subject, alcohol or drug consumption, caffeine or nicotine intake and circadian rhythms, and the subject's apolipoprotein epsilon (ApoE) genotype to name a few.

Increased risk can also be determined from p-values that are derived using logistic regression. Binomial (or binary) logistic regression is a form of regression that is used when the dependent is a dichotomy and the independents are of any type. Logistic regression can be used to predict a dependent variable on the basis of continuous and/or categorical independents and to determine the percent of variance in the dependent variable explained by the independents; to rank the relative importance of independents; to assess interaction effects; and to understand the impact of covariate control variables. Logistic regression applies maximum likelihood estimation after transforming the dependent into a "logit" variable (the natural log of the odds of the dependent occurring or not). In this way, logistic regression estimates the probability of a certain event occurring. These analyses are conducted with the program SAS.

SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and non-parametric analysis.

Accordingly, select embodiments of the present invention comprise the use of a computer comprising a processor and the computer is configured or programmed to generate one or more PUFA profiles and/or to determine statistical risk. The methods may also comprise displaying the one or more profiles and/or risk profiles on a screen that is communicatively connected to the computer. In another embodiment, two different computers can be used: one computer configured or programmed to generate one or more PUFA profiles and a second computer configured or programmed to determine statistical risk. Each of these separate computers can be communicatively linked to its own display or to the same display.

The assessment for flux of the one or more PUFAs can be expressed as absolute or relative values and may or may not be expressed in relation to another component, a standard an internal standard or another molecule of compound known to be in the sample. If flux is assessed as relative to a standard or internal standard, the standard may be added to the test sample prior to, during or after sample processing.

The subject's flux measurement(s) is(are) compared to flux measurements deemed to be normal. To establish influx in a normal individual, an individual or group of individuals may be first assessed for their ability to recall past events to establish that the individual or group of individuals has a normal or acceptable ability memory. Such individuals would be followed serially in a longitudinal study that documents their lack of development of memory disturbances over at least a 5-year period. Such stable cognitive status and the correlated PUFA flux levels taken serially over this time in the individual or group of individuals would establish a "normal PUFA flux level." In one embodiment, normal flux levels can be ascertained from the same subject when the subject is deemed to possess normal cognitive abilities and no signs (clinical or otherwise) of memory impairment. In one embodiment, normal flux levels are assessed in the same subject from whom the sample is taken prior to the onset of measureable, perceivable or diagnosed memory impairment. That is, the term "normal" with respect to PUFA flux can be used to mean the subject's baseline PUFA flux prior to the onset of memory impairment. The PUFA flux levels can then be reassessed serially and compared to either the subject's baseline PUFA flux level, or to the mean PUFA flux level of subjects followed for a minimum of 5 years that maintained normal cognitive status.

Thus, the present invention also include methods of monitoring the progression of memory impairment or brain injury in a subject, with the methods comprising determining the subject's PUFA influx levels more than once over a period of time. For example, some embodiments of the methods of the present invention will comprise determining the subject's PUFA influx levels two, three, four, five, six, seven, eight, nine, 10 or even more times over a period of time, such as a year, two years, three, years, four years, five years, six years, seven years, eight years, nine years or even 10 years or longer.

The methods of the present invention would also include embodiments in which the subject's influx levels are assessed during and after treatment of memory impairment and/or brain injury. In other words, the present invention also includes methods of monitoring the efficacy of treatment of memory impairment or monitoring methods of treating brain injury by assessing the subject's influx levels over the course of the treatment and after the treatment. The treatment may be any treatment designed to increase a subject's ability to recall past events, i.e., improve a subject's memory, or to alleviate the symptoms of the brain injury.

In another embodiment, normal influx levels are assessed in a sample from a different subject or patient (from the subject being analyzed) and this different subject does not have or is not suspected of having memory impairment or brain injury. In still another embodiment, normal influx levels are assessed in a population of healthy individuals, the constituents of which display no memory impairment or brain injury. Thus, the subject's influx levels can be compared to normal influx levels generated from a single normal sample or normal influx levels generated from more than one normal subject sample.

If it is determined that a subject has an increased risk of memory impairment, the attending health care provider may subsequently prescribe or institute a treatment program. In this manner, the present invention also provides for methods of screening individuals as candidates for treatment of memory impairment. The attending healthcare worker may begin treatment, based on the subject's influx levels, before there are perceivable, noticeable or measurable signs of memory impairment in the individual.

Similarly, the invention provides methods of treating memory impairment in a subject in need thereof. The treatment methods include obtaining a subject's PUFA or composite profile as defined herein and prescribing a treatment regimen to the subject if the PUFA and/or composite profile indicate that the subject is at risk of suffering from memory impairment.

The methods of treatment also include methods of monitoring the effectiveness of a treatment for memory impairment. Once a treatment regimen has been established, with or without the use of the methods of the present invention to assist in a diagnosis of memory impairment, the methods of monitoring a subject's PUFA or composite profile over time can be used to assess the effectiveness of a memory impairment treatment. Specifically, the subject's PUFA or composite profile can be assessed over time, including before, during and after treatments for memory impairment. The PUFA or composite profile can be monitored, with, for example, the normalization or decline in the values of the profile over time being indicative that the treatment may showing efficacy or may lead to improvement in the subjects memory and/or cognitive abilities.

Suitable treatments for memory impairment that may be initiated in response to an indication that the subject is at risk of suffering from memory impairment include but are not limited to prescribing or administering fenofibrate, cholinesterase inhibitors and memantine to the subject. Specific examples of cholinesterase inhibitors include but are not limited to donepezil, rivastigmine and galantamine. Another treatment includes but is not limited to SOUVENAID™, which is a mixture of omega-3 fatty acids, choline, uridine monophosphate and a mixture of antioxidants and B vitamins. Other treatments for memory impairment that can be used in conjunction with the present invention include consumption of coconut oil, ginger, green tea, fatty fish, cold-water fish such as but not limited to salmon, tuna, trout, mackerel and sardines, soy products, blueberries and other dark berries, green leafy vegetables and cruciferous vegetables such as but not limited to broccoli.

All patents and publications mentioned in this specification are indicative of the level of those skilled in the art to which the invention pertains. All patents and publications cited herein are incorporated by reference to the same extent as if each individual publication was specifically and individually indicated as having been incorporated by reference in its entirety

EXAMPLES

Example 1

Neurocognitive Methods

A total of 525 volunteers participated in this study as part of the Rochester/Orange County Aging Study (R/OCAS), an ongoing natural history study of cognition in community-dwelling older adults. Briefly, participants were followed with yearly cognitive assessments and blood samples were collected following an overnight fast and withholding of all medications. At baseline and each yearly visit, participants completed assessments in such as activities in daily living, memory complaints, signs and symptoms of depression, and were administered a detailed cognitive assessment.

For this study, data from the cognitive tests were used to classify participants into groups for biomarker discovery.

Standardized scores (Z-scores) were derived for each participant on each cognitive test and the composite Z-scores were computed for five cognitive domains (attention, executive, language, memory, visuoperceptual) (Table).

TABLE 1

| Attention ($Z_{att}$) | Executive ($Z_{exe}$) | Language ($Z_{lan}$) | Visuoperceptual ($Z_{vis}$) | Memory ($Z_{mem}$) |
|---|---|---|---|---|
| Wechsler Memory Scale-III Forward Digit Span (WMS-III FDS) | Wechsler Memory Scale-III Backward Digit Span (WMS-III BDS) | 1-min Category fluency (Animals) | Hooper Visual Organization Test (HVOT) | Rey Auditory Verbal Learning Test Learning (RAVLT Learning) |
| Trail Making Test-Part A (TMT-A) | Trail Making Test-Part B (TMT-B) | Boston Naming Test 60-Item version (BNT-60) | | Rey Auditory Verbal Learning Test Retrieval (RAVLT Retrieval) Rey Auditory Verbal Learning Test Retention (RAVLT Recognition) |

Normative data for Z-score calculations were derived from the performance of the participants on each of the cognitive tests adjusted for age, education, sex, and visit. To reduce the effect of cognitively impaired participants on the mean and SD, age-, education-, sex, and visit-adjusted residuals from each domain Z-score model were robustly standardized to have median 0 and robust SD=1, where the robust SD=IQR/1.35, as 1.35 is the IQR (Inter-Quartile Range) of a standard normal distribution.

The participants were then categorized into groups of incident aMCI or early AD (combined into one category aMCI/AD), cognitively normal control (NC), and those who converted to MCI or AD over the course of the study (Converters) based on these composite scores. Impairment was defined as a Z-score 1.35 SD below the cohort median. All participants classified as aMCI met recently revised criteria for the amnestic subtype of MCI. Other behavioral phenotypes of MCI were excluded to concentrate on the amnestic form, which most likely represents nascent Alzheimer's pathology. All early AD participants met recently revised criteria for probable Alzheimer's disease with impairment in memory and at least one other cognitive domain. For the MCI and early AD groups, scores on the measures of memory complaints (MMQ) and activities of daily living (PGC-IADL) were used to corroborate research definitions of these states. All Converters had non-impaired memory at entry to the study ($Z_{mem} \geq -1.35$), developed memory impairment over the course of the study ($Z_{mem} \leq -1.35$) and met criteria for the above definitions of aMCI or AD. To enhance the specificity of the biomarker analyses, NC participants in this study were conservatively defined with $Z_{mem} \pm 1$ SD of the cohort median rather than simply $\geq -1.35$, and all other Z-scores $\geq -1.35$ SD.

For each subject, $Z_{mem}$(last), $Z_{att}$(last), $Z_{exe}$(last), $Z_{lan}$(last), and $Z_{vis}$(last) were defined as the age-gender-education-visit-adjusted robust Z-scores for the last available visit for each subject. The aMCI/AD group was defined as those participants whose adjusted $Z_{mem}$ was 1 IQR below the median at their last available visit, i.e., $Z_{mem}$(last) $\leq -1.35$. Converters were defined as that subset of the a MCI/AD group whose adjusted $Z_{mem}$ at baseline visit 0 was no more than 1 IQR below the median, i.e., $Z_{mem}$(visit=0) $>-1.35$ and $Z_{mem}$(last) $\geq -1.35$. Participants were classified as NC if they had central scores on all domains at both the first and last visits, i.e., only if they met all of the following six conditions: (i) $-1<Z_{mem}$(last)$<1$, (ii) $-1<Z_{mem}$(visit=0)$<1$, (iii) $Z_{min}$(last) $>-1.35$, (iv) $Z_{min}$(visit=0) $>-1.35$, (v) $Z_{max}$(last)$<1.35$, and (vi) $Z_{max}$(visit=0)$<1.35$, where $Z_{max}$(last) and $Z_{max}$(visit=0) denote the maximum of the five adjusted Z-scores at the last and first visits, respectively. $Z_{mem}$ for normal participants had to be within 0.74 IQR (1 SD) of the median, rather than just 1 IQR (1.35 SD), to guarantee that they were >0.25 IQR (0.35 SD) from aMCI/AD participants.

After three years of being in the study, (December, 2010), 202 participants had completed a baseline and two yearly visits. At the third visit, 53 participants met criteria for a MCI/AD and 96 met criteria for NC. Of the 53 aMCI/AD participants, 18 were Converters and 35 were incident aMCI or AD. The remaining 53 participants did not meet the criteria for either group and were not considered for biomarker profiling. Some of these individuals met criteria for non-amnestic MCI and many had borderline or even above average memory scores that precluded their inclusion as either a MCI/AD or NC. 53 of the NC participants were matched to the 53 aMCI/AD participants based on sex, age, and education level. Blood samples were obtained on the last available study visit for the 53 MCI/AD and the 53 NC for biomarker discovery. Two blood samples from each of the 18 Converters were also included: one from the baseline visit (Converter$_{pre}$) when $Z_{mem}$ was non-impaired and one from the third visit (Converter$_{post}$) when $Z_{mem}$ was impaired and they met criteria for either aMCI or AD. Thus, at total of 124 samples from 106 participants were analyzed.

Internal cross-validation was employed to validate findings from the discovery phase. Blood samples for validation were identified at the end of the fifth year of the study and all 106 participants included in the discovery phase were excluded from consideration for the validation phase. Cognitive composite Z-scores were re-calculated based on the entire sample available and the same procedure and criteria were used to identify samples for the validation phase. A total of 145 participants met criteria for a group: 21aMCI/AD and 124 NC. Of the 21 aMCI/AD, 10 were Converters. 20 of the NC participants were matched to the aMCI/AD participants on the basis of age, sex, and education level as in the discovery phase. In total, 41 participants contributed samples to the validation phase and, as before, the 10 Converters also contributed a baseline sample (Converter$_{pre}$) for a total of 51 samples.

Neurocognitive Statistical Analyses

The neurocognitive analyses were designed to demonstrate the general equivalence of the discovery and validation samples on clinical and cognitive measures. Separate Multivariate Analysis of Variance (MANOVA's) tests were used to examine discovery/validation group performance on the composite Z-scores and on self-report measures of memory complaints, memory related functional impairment, depressive symptoms, and a global measure of cognitive function. In the first MANOVA, biomarker sample (discovery, validation) was the independent variable and MMQ, IADL, GDS, and MMSE were the dependent variables. In the second MANOVA, biomarker sample (discovery, validation) was the independent variable and the five cognitive domain Z-scores ($Z_{att}$, $Z_{exe}$, $Z_{lan}$; $Z_{mem}$, and $Z_{vis}$) were the dependent variables. Significance was set at alpha=0.05 and Tukey's HSD procedure was used for post-hoc comparisons. All statistical analyses were performed using SPSS (version 21).

Example 2

Lipidomics Methods

LC/MS-grade acetonitrile (ACN), Isopropanol (IPA), water and methanol were purchased from Fisher Scientific (New Jersey, USA). High purity formic acid (99%) was purchased from Thermo-Scientific (Rockford, Ill.). Debrisoquine, 4-Nitrobenzoic acid (4-NBA), Pro-Asn, Glycoursodeoxycholic acid, Malic acid, were purchased from Sigma (St. Louis, Mo., USA). All lipid standards including 14:0 LPA, 17:0 Ceramide, 12:0 LPC, 18:0 Lyso PI and PC(22:6/0:0) were procured from Avanti Polar Lipids Inc. (USA).

Metabolite Extraction

Briefly, the plasma samples were thawed on ice and vortexed. For metabolite extraction, 25 μL of plasma sample was mixed with 175 μL of extraction buffer (25% acetonitrile in 40% methanol and 35% water) containing internal standards [10 μL of debrisoquine (1 mg/mL), 50 μL of 4, nitrobenzoic acid (1 mg/mL), 27.3 μl of Ceramide (1 mg/mL) and 2.5 μL of LPA (lysophosphatidic acid) (4 mg/mL) in 10 mL]. The samples were incubated on ice for 10 minutes and centrifuged at 14,000 rpm at 4° C. for 20 minutes. The supernatant was transferred to a fresh tube and dried under vacuum. The dried samples were reconstituted in 200 μL of buffer containing 5% methanol, 1% acetonitrile and 94% water. The samples were centrifuged at 13,000 rpm for 20 minutes at 4° C. to remove fine particulates. The supernatant was transferred to a glass vial for UPLC-ESI-Q-TOF-MS analysis.

UPLC-ESI-QTOF-MS Based Data Acquisition for Untargeted Lipidomic Profiling

Each sample (2 μL) was injected onto a reverse-phase CSH C18 1.7 μM 2.1×100 mm column using an Acquity H-class UPLC system (Waters Corporation, USA). The gradient mobile phase comprised of water containing 0.1% formic acid solution (Solvent A), 100% acetonitrile (Solvent B) and 10% acetonitrile in isopropanol (IPA) containing 0.1% formic acid and 10 mM Ammonium formate (Solvent C). Each sample was resolved for 13 minutes at a flow rate of 0.5 mL/min for 8 min and then 0.4 mL/min from 8 to 13 min. The UPLC gradient consisted of 98% A and 2% B for 0.5 min then a ramp of curve 6 to 60% B and 40% A from 0.5 min to 4.0 min, followed by a ramp of curve 6 to 98% B and 2% A from 4.0 to 8.0 min, then ramped to 5% B and 95% C from 9.0 min to 10.0 min at a flow rate of 0.4 ml/min, and finally to 98% A and 2% B from 11.0 min to 13 minutes. The column eluent was introduced directly into the mass spectrometer by electrospray ionization. Mass spectrometry was performed on a Quadrupole-Time of Flight (Q-TOF) instrument (Xevo G2 QTOF, Waters Corporation, USA) operating in either negative ($ESI^-$) or positive ($ESI^+$) electrospray ionization mode with a capillary voltage of 3200 V in positive mode and 2800 V in negative mode, and a sampling cone voltage of 30 V in both modes. The desolvation gas flow was set to 750 L $h^{-1}$ and the temperature was set to 350° C. while the source temperature was set at 120° C. Accurate mass was maintained by introduction of a lock spray interface of leucine-enkephalin (556.2771 $[M+H]^+$ or 554.2615 $[M-H]^-$) at a concentration of 2 pg/μl in 50% aqueous acetonitrile and a rate of 2 μl/min. Data were acquired in centroid MS mode from 50 to 1200 m/z mass range for TOF-MS scanning as single injection per sample and the batch acquisition was repeated to check experimental reproducibility. For the metabolomics profiling experiments, pooled quality control (QC) samples (generated by taking an equal aliquot of all the samples included in the experiment) were run at the beginning of the sample queue for column conditioning and every ten injections thereafter to assess inconsistencies that are particularly evident in large batch acquisitions in terms of retention time drifts and variation in ion intensity over time. This approach has been recommended and used as a standard practice by leading metabolomics researchers. A test mix of standard metabolites was run at the beginning and at the end of the run to evaluate instrument performance with respect to sensitivity and mass accuracy. The overlay of the total ion chromatograms of the quality control samples depicted excellent retention time reproducibility. The sample queue was randomized to remove bias. The TICs for each of the three groups showed characteristic patterns.

Stable Isotope Dilution—Multiple Reaction Monitoring Mass Spectrometry (SID-MRM-MS)

Targeted metabolomic analysis of plasma sample was performed using the Biocrates Absolute-IDQ P180 (BIOCRATES, Life Science AG, Innsbruck, Austria). This validated targeted assay allows for simultaneous detection and quantification of metabolites in plasma samples (10 μL) in a high throughput manner. The methods have been described in detail. The plasma samples were processed as per the instructions by the manufacturer and analyzed on a triple quadrupole mass spectrometer (Xevo TQ-S, Waters Corporation, USA) operating in the MRM mode. The measurements were made in a 96 well format for a total of 148 samples, seven calibration standards and three quality control samples were integrated in the kit.

Briefly, the flow injection analysis (FIA) tandem mass spectrometry (MS/MS) method was used to quantify a panel of 144 lipids simultaneously by multiple reaction monitoring. Absolute quantification was achieved by extrapolating from a standard curve. The other metabolites were resolved on the UPLC and quantified using scheduled MRMs. The kit facilitated absolute quantitation of 21 amino acids, hexose, carnitine, 39 acylcarnitines, 15 sphingomyelins, 90 phosphatidylcholines and 19 biogenic amines. Data analysis was performed using the MetIQ software (Biocrates) while the statistical analyses were performed using the STAT pack module v3 (Biocrates). The abundance was calculated from area under the curve by normalizing to the respective isotope labeled internal standard. The concentration is expressed as nmol/L. Quality control samples were used to assess reproducibility of the assay. The mean of the coefficient of variation (CV) for the 180 metabolites was 0.08 and 95% of the metabolites had a CV of <0.15.

Lipidomics Statistical Analyses

The m/z features of metabolites were normalized with log transformation that stabilized the variance followed with a quantile normalization to make the empirical distribution of intensities the same across samples. The metabolites were selected among all those known to be identifiable using a ROC regularized learning technique, based on the least absolute shrinkage and selection operator (LASSO) penalty as implemented with the R package 'glmnet', which uses cyclical coordinate descent in a pathwise fashion. The regularization path over a grid of values was obtained for the tuning parameter lambda through 10-fold cross-validation. The optimal value of the tuning parameter lambda, which was obtained by the cross-validation procedure, was then used to fit the model. All the features with non-zero coefficients were retained for subsequent analysis. The classification performance of the selected metabolites was assessed using area under the ROC (receiver operating characteristic) curve (AUC). The ROC can be understood as a plot of the probability of classifying correctly the positive samples against the rate of incorrectly classifying true negative samples. Thus the AUC measure of an ROC plot is actually a measure of predictive accuracy. To maintain rigor of independent validation, the simple logistic model with the ten metabolite panel was used, although a more refined model can yield greater AUC.

Results

Over the course of the study, 74 participants met criteria for either aMCI or mild AD, 46 of these were incidental cases at entry and 28 phenoconverted (Converters) from a non-impaired memory status at entry (Converter$_{pre}$). The average time to phenoconversion was 2.1 years (range=1-5 years). 53 aMCI/AD participants were selected, including 18 Converters, and 53 age-, education-, and sex-matched cognitively normal control (NC) participants for untargeted lipidomics biomarker discovery. Internal cross validation was used to evaluate the accuracy of the discovered PUFA profile in classifying a blinded sample of 51 subjects consisting of the remaining subset of 21 aMCI/AD participants, including 10 Converters, and an additional 20 matched NC.

The aMCI/AD, Converter, and NC groups were defined primarily using a composite measure of memory performance in addition to composite measures of other cognitive abilities and clinical measures of memory complaints and functional capacities. (See Tables 1 and 2).

TABLE 2

| Clinical/Cognitive Measures | Dependent Measure (Range) | Domain Assessed |
|---|---|---|
| Multiple Assessment Inventory IADL Scale (MAI-IADL) Lawton M P. (1988) Instrumental Activities of Daily Living (IADL) scale: Original observer-rated version. *Psychopharmacology Bulletin*, 24, 785-7. | Total Score (0-27) | Functional capacities |
| Multifactorial Memory Questionnaire (MMQ) Troyer A K and Rich J B. (2002). Psychometric properties of a new metamemory questionnaire for older adults. *Journal of Gerontology*, 57(1), 19-27. | Total Score (0-228) | Memory complaints |
| Mini Mental State Examination (MMSE) Folstein, M F, Folstein, S E, and McHugh, P R. (1975). "Mini-mental state". *Journal of Psychiatric Research*, 12, 189-98. | Total Score (0-30) | Global cognitive ability |
| Geriatric Depression Scale-Short Form (GDS-SF) Sheikh J I and Yesavage J A. (1986). Geriatric Depression Scale (GDS): Recent evidence and development of a shorter version. *Clinical Gerontologist*, 5, 165-173. | Total Score (0-15) | Mood |
| Wechsler Memory Scale-III Forward Digit Span (WMS-III FDS) Wechsler D. *Wechsler Memory Scale-III Manual*. San Antonio, TX: The Psychological Corporation, 1997. | Span Length (0-9) | Attention |
| Trail Making Test-Part A (TMT-A) Reitan R M. (1958). Validity of the Trail Making Test as an indicator of organic brain damage. *Perceptual and Motor Skills*, 8, 271-6. | Completion time (1-300 seconds) | Attention |
| Wechsler Memory Scale-III Backward Digit Span (WMS-III BDS) Wechsler D. *Wechsler Memory Scale-III Manual*. San Antonio, TX: The Psychological Corporation, 1997. | Span Length (0-8) | Executive ability |
| Trail Making Test-Part B (TMT-B) Reitan R M. (1958). Validity of the Trail Making Test as an indicator of organic brain damage. *Perceptual and Motor Skills*, 8, 271-6. | Completion Time (1-300 seconds) | Executive ability |
| Category fluency (Animals) Borkowski J, Benton A, Spreen O. (1967). Word fluency and brain damage. *Neuropsychologia*, 5, 135-140 | Animals named in 1-minute | Language |
| Boston Naming Test 60-Item version (BNT-60) Kaplan E, Goodglass H, and Weintraub S. (1983). Boston Naming Test. Philadelphia: Lea & Feibiger. | Total Correct (0-60) | Language |
| Rey Auditory Verbal Learning Test Learning (RAVLT Learning) Rey A. (1964). L'examen clinique en psychologie. Paris: Presses Universitaires de France. | Total words recalled over Trials 1-5 (0-75) | Verbal learning |
| Rey Auditory Verbal Learning Test Recall (RAVLT Retrieval) Rey A. (1964). L'examen clinique en psychologie. Paris: Presses Universitaires de France. | Words recalled at 20-minute delay (0-15) | Verbal retrieval |
| Rey Auditory Verbal Learning Test Retention (RAVLT Recognition) Rey A. (1964). L'examen clinique en psychologie. Paris: Presses Universitaires de France. | True positives-false positives (0-15) | Verbal retention |

TABLE 2-continued

| Clinical/Cognitive Measures | Dependent Measure (Range) | Domain Assessed |
|---|---|---|
| Hooper Visual Organization Test (HVOT) Hooper H E. Hooper Visual Organization Test (VOT) Los Angeles: Western Psychological Services; 1983. | Total score (0-30) | Visuoperception |

Figure 1:
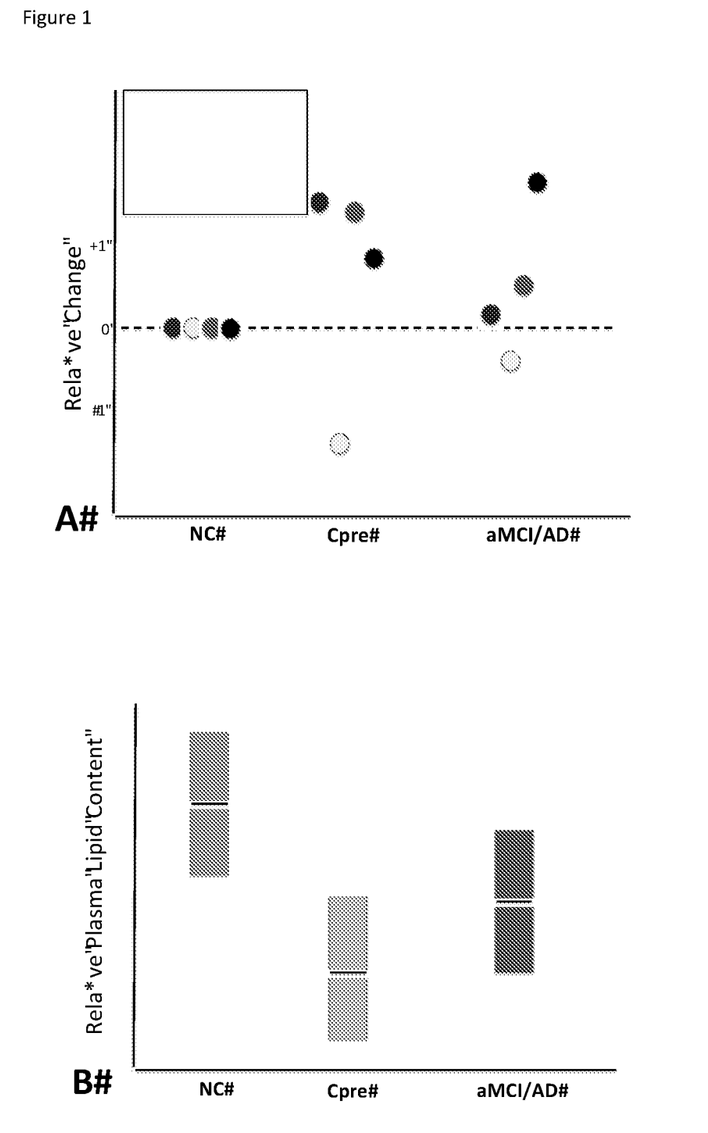

Plots of group means on the composite measures can be found in FIG. 1 and group means are reported in Table 3. The discovery and validation groups did not differ on clinical measures including self-reported memory complaints, functional impairment, depressive symptoms, and a global measure of cognition ($F_{(4,170)}=1.376$, $p=0.244$), nor on any composite Z-score ($F_{(5,169)}=2.118$, $p=0.066$) demonstrating the general equivalence of the participants used for the discovery and validation phases of the biomarker analysis.

TABLE 3

| Cognitive Measure | Normal Control (n = 73) | Converter$_{pre}$ (n = 28) | MCI/ AD (n = 74) |
|---|---|---|---|
| Multiple Assessment Inventory IADL Scale (MAI-IADL) | 26.51 (1.71) | 26.65 (0.87) | 24.82 (3.60) |
| Multifactorial Memory Questionnaire (MMQ) | 130.32 (19.93) | 139.71 (13.36) | 121.01 (18.14) |
| Mini Mental State Examination (MMSE) | 28.64 (1.30) | 28.61 (2.49) | 26.32 (2.87) |
| Geriatric Depression Scale-Short Form (GDS-SF) | 1.47 (2.02) | 1.32 (2.28) | 1.97 (2.7) |
| Wechsler Memory Scale-III Forward Digit Span (WMS-III FDS) | 6.25 (1.05) | 6.18 (0.95) | 6.14 (1.13) |
| Trail Making Test-Part A (TMT-A) | 36.69 (13.23) | 46.14 (14.75) | 55.26 (44.63) |
| Wechsler Memory Scale-III Backward Digit Span (WMS-III BDS) | 4.34 (0.9) | 4.29 (0.76) | 4.01 (0.91) |
| Trail Making Test-Part B (TMT-B) | 98.53 (41.30) | 134.57 (63.89) | 151.99 (69.82) |
| Category fluency (Animals) | 20.91 (4.72) | 19.0 (5.24) | 15.16 (5.03) |
| Boston Naming Test 60-Item version (BNT-60) | 56.29 (3.19) | 53.14 (7.96) | 50.51 (9.46) |
| Rey Auditory Verbal Learning Test Learning (RAVLT Total Learning A1-A5) | 43.43 (7.76) | 37.0 (5.88) | 27..08 (7.01) |
| Rey Auditory Verbal Learning Test Delayed Recall (RAVLT Trial A7) | 7.84 (2.48) | 5.32 (2.59) | 1.93 (1.64) |
| Rey Auditory Verbal Learning Test Retention (RAVLT Recognition) | 13.30 (1.57) | 11.14 (2.24) | 7.09 (3.15) |
| Hooper Visual Organization Test (HVOT) | 23.96 (3.05) | 22.36 (3.72) | 20.93 (4.51) |

Lipidomic Definition of Participant Groups

The plasma samples from the 124 discovery phase participants were subjected to lipidomics analysis. In the discovery phase, metabolomic/lipidomic profiling yielded 2700 features in the positive mode and 1900 features in the negative mode. The metabolites that define the participant groups were selected from among all known to be identifiable using a regularized learning technique, the least absolute shrinkage and selection operator (LASSO) penalty as implemented with the R package 'glmnet'. The LASSO analysis revealed features that assisted in unambiguous class separation between aMCI/AD, Converter$_{pre}$ and the NC group (Table 4).

TABLE 4

Putative metabolite markers resulting from binary comparison of the study groups

| Metabolite | Lasso Coefficient | Comparison Groups | Mode | Mass/ Charge Ratio |
|---|---|---|---|---|
| PI(18:0/0:0) | ↓ (−0.674) | Normal vs Converter$_{pre}$ | NEG | 599.3226 |
| Pro Asn | ↑ (0.192) | Normal vs aMCI/AD | POS | 230.1146 |
| Glycoursode-oxycholic acid | ↑ (0.107) | Normal vs aMCI/AD | POS | 450.3196 |
| Malic acid | ↓ (−0.024) | Normal vs aMCI/AD | POS | 134.0207 |

The markers in Table 1 were chosen based on the significant predictive value as determined by LASSO coefficient analysis. The positive estimated LASSO coefficient suggests elevation in corresponding comparison group (aMCI/AD and Converter$_{pre}$) compared to normal control (NC) participants. Up arrows indicate up-regulation in the comparison group as compared to the NC participants while the down arrow suggests down-regulation in these groups.

This untargeted lipidomic analysis revealed a significant decrease in the level of phosphatidyl inositol (PI) in the Converter$_{pre}$ group and an elevation in the plasma levels of glycoursodeoxycholic acid in the aMCI/AD patients as compared to the NC group. These metabolites were unambiguously identified using tandem mass spectrometry. The other metabolites that displayed differential abundance in the study groups consisted of amino acids, biogenic amines and a broad range of phospholipids and other lipid species that were putative identified based on accurate mass stringency of ≤5 ppm.

In the next step of the metabolomic/lipidomic analyses, multiple reaction monitoring (MRM) was performed for stable isotope dilution-mass spectrometry (SID-MS) to unambiguously identify and quantify those metabolites such as lipids, amino acids and biogenic amines that function similar to those identified in the LASSO analysis and characterize the participant groups, with special emphasis on differences that would predict a predisposition of phenoconversion from NC to aMCI/AD. The data revealed significantly lower plasma levels of serotonin, taurine, phenylalanine, proline, lysine, phosphatidyl choline (PC) and acylcarnitine (AC) in Converter$_{pre}$ participants who later developed aMCI/AD. Conversely, these participants also showed an elevation in the levels of DOPA.

TABLE 5

Difference detection of putative metabolites using stable isotope dilution multiple reaction monitoring mass spectrometry (SID-MRM-MS).

| Metabolite | Fold Change | Comparison Groups | Mode | p-value |
|---|---|---|---|---|
| PC ae C38:4 | ↓ | Normal vs Converter$_{pre}$ | POS | 0.00417 |
| Praline | ↓ | Normal vs Converter$_{pre}$ | POS | 3.00E−05 |
| Lysine | ↓ | Normal vs Converter$_{pre}$ | POS | 0.0020 |

TABLE 5-continued

Difference detection of putative metabolites using stable isotope dilution multiple reaction monitoring mass spectrometry (SID-MRM-MS).

| Metabolite | Fold Change | Comparison Groups | Mode | p-value |
|---|---|---|---|---|
| Serotonin | ↓ | Normal vs Converter$_{pre}$ | POS | 0.0160 |
| Taurine | ↓ | Normal vs Converter$_{pre}$ | POS | 0.0030 |
| DOPA | ↑ | Normal vs Converter$_{pre}$ | POS | 0.0001 |
| Phenylalanine | ↓ | Normal vs Converter$_{pre}$ | POS | 1.00E−05 |
| Acylcarnitine C7-DC | ↓ | Normal vs aMCI/AD | POS | 0.0001 |

Up arrows in Table 5 indicate up-regulation in the comparison group as compared to the normal control (NC) participants while the down arrow suggests down-regulation in these groups.

The targeted metabolomic/lipidomic analysis identified of a set of ten metabolites, comprised of PCs, lyso PCs, and ACs that were depleted in the plasma of the Converter$_{pre}$ participants compared to the NC group. These metabolites remain depleted after the same participants phenoconverted to aMCI/AD (Converters$_{post}$) and were nearly equivalent to the low levels seen in the cognitively impaired aMCI/AD group. A simple logistic model with the ten metabolite panel was used to predict/classify Converter$_{pre}$ and NC participants. When displayed as a ROC curve, the ten metabolite panel comparing Converter$_{pre}$ and NC participants yielded an AUC of 0.96, while the panel yielded an AUC of 0.827 for the aMCI/AD vs NC classification.

To confirm the reproducibility of the ten metabolite panel from the discovery samples, targeted quantitative metabolomics/lipidomics analyses was performed using plasma from the independent validation group of 40 participants as an independent cross validation. One sample from the MCI/AD group was not available for lipidomic analysis. The validation samples were obtained from the last available visit from the aMCI/AD, Converter$_{pre}$, and NC groups and were designated as groups A, B, and C and analyzed in a blinded fashion, without specification of diagnostic identities. The samples were processed and analyzed using the same SID-MRM-MS technique as in the discovery phase. The blinded data were analyzed to determine if the unknown groups could be characterized into the correct diagnostic categories based solely on the levels of the ten metabolite panel. The validation analysis revealed lower levels of the assayed metabolites in groups A and B compared to group C. Based on these qualitative differences, it was predicted that group C was the NC group and groups A and B were Converter$_{pre}$ and aMCI/AD groups, respectively. Subsequent un-blinding of the groups confirmed these predictions.

The metabolomic data was used from the untargeted LASSO analysis to build separate linear classifier models that would distinguish the aMCI/AD group from the NC group and the Converter$_{pre}$ group from the NC group. A receiver operating characteristic (ROC) analysis was employed to determine the area under the ROC curve (AUC) to assess the performance of the classifier models in differentiating the groups. When distinguishing between the Converter$_{pre}$ and NC groups, the LASSO identified metabolites yielded an AUC of 0.96, and 0.83 when distinguishing the aMCI/AD and NC groups. These high AUC values demonstrate robust discrimination between the aMCI/AD, Converter$_{pre}$, and NC groups by the models. Using the same linear classifier method, a simple logistic model was constructed using just the ten metabolite panel and used this to classify the same groups. When displayed as a ROC curve, the ten metabolite panel classified Converter$_{pre}$ and NC participants with an AUC of 0.96, while the panel yielded an AUC of 0.827 for the aMCI/AD vs NC classification.

The effect of apolipoprotein E (APOE) genotype was considered. ApoE protein is involved in lipid transport/metabolism and APOE allele status, including homozygous (ε2/2 vs. ε3/3 vs. ε4/4) and heterozygous (ε2/3 vs. ε2/4 vs. ε3/4) options, alter the risk for Alzheimer's Disease (AD). With the presence of at least a single APOE ε4 allele increasing the risk for AD (with an even greater risk with ε4/4), risk status was accounted for by repeating this classification analysis with the −ε4 allele presence as a covariate. This latter analysis found the classification accuracy changed only minimally from 0.96 to 0.968 (p=0.992). Furthermore, a classifier model using only APO −ε4 produced an AUC of 0.54 for classifying the Converter$_{pre}$ and NC groups implying virtually random classification. These findings clearly indicate that the presumed pathophysiology reflected by the ten metabolite biomarker panel is independent of ApoE mediated effects. Finally, the same simple logistic classifier model developed for the discovery samples was applied to the independent validation samples. The ROC constructed from the validation group data classified Converter$_{pre}$ and NC participants with an AUC of 0.92 and 0.77 for classifying the aMCI/AD vs NC groups. For a specificity of 90%, the ten metabolite panel yielded a sensitivity of 83.3% for correct classification of the Converter$_{pre}$ and NC participants in the discovery phase and a sensitivity of 90% in the validation phase.

Example 3

Methods for Preclinical Alzheimer's Disease Index (PADI)

All participants were community-dwelling, older adults from the greater Rochester, N.Y. and Irvine, Calif. communities. Participants were recruited through local media (newspaper and television advertisements), senior organizations, and word of mouth. Inclusion criteria included age 70 or older, proficiency with written and spoken English and corrected vision and hearing necessary to complete the cognitive battery. Participants were excluded for the presence of known major psychiatric or neurological illness (including Alzheimer's disease or MCI, cortical stroke, epilepsy, and psychosis) at time of enrollment, current or recent (<1 month) use of anticonvulsants, neuroleptics, HAART, antiemetics, and antipsychotics for any reason, and serious blood diseases including chronic abnormalities in complete blood count and anemia requiring therapy and/or transfusion.

Operationalizing Groups

Alzheimer's disease is a cognitive disorder defined in numerous diagnostic schemes by a primary impairment in memory. The classification of preclinical Alzheimer's disease via PADI relies heavily on the assessment of memory, but it is recognized that the preclinical state may also involve other cognitive domains, thus the methods disclosed herein rely on assessing all primary cognitive domains (Table 6). The primary Memory outcome was based on the Rey Auditory Visual Learning Test (RAVLT). Learning was defined as the sum of the number of correct words recalled over the 5 learning trials; Retrieval was defined as the total number of correct words recalled from trial A7; and Retention was defined as the total number correct words recognized minus the number of false positives. Each of these three sub-scores (Learning, Retrieval, and Retention) was converted to an empirical Z-score by subtracting its sample mean and dividing by its sample SD. The three resulting positively correlated RAVLT-based Z-scores were then averaged to form the composite Memory score (Zmem). So defined, Zmem was approximately normal with mean 0, SD<1, and some negative skewness attributable to the fact that healthy participants often score at or near the upper bounds, especially for Retention. The Attention (Zatt), Executive (Zexe), and Language (Zlan) scores were each defined as averages of empirical Z-score transforms of pairs of subscores, as follows. Zatt: (1) completion time (in seconds, truncated at 300 s) for the Trail Making Test Part A and (2) the Wechsler Memory Scale-III Forward Digit Span; Zexe: (1) completion time (in seconds, truncated at 300 s) for the Trail Making Test Part B and (2) the Wechsler Memory Scale-III Backward Digit Span; Zlan: (1) total score (out of 60) for the Boston Naming Test and (2) Category Fluency (Animals Named in 1 minute). The Visuo-perceptual score (Zvis) was simply the empirical Z-transform of the Total Score (out of 30) for the Hooper Visual Organization Test (HVOT), which itself was approximately normally distributed. See Table 2 for composite Z score components.

Standardization and Adjustment for Age, Gender, Education, and Visit

Linear Generalized Estimating Equation (GEE) models were used to model each of the five cognitive domains (Memory, Attention, Executive, Language, and Visuospatial) as a function of age, gender, education, and visit number, using a homoscedastic working independence covariance matrix, i.e., least squares was used to estimate all linear model coefficients based on the pooled data from all available visits. Since Memory was the focal cognitive domain, the functional form for the covariates was selected to best model Memory, and exactly the same functional form was used for the other four cognitive domains. Given the evidence of nonlinearity, the effect of education was modeled using a continuous piecewise linear spline with knots at 12, 14, and 16 years of education. Memory increased with years of education between 5-12 years, decreased between 12-14 years, increased again between 14-16 years, and then nearly leveled off for 16-23 years. Age was modeled linearly, as there was insufficient evidence to support nonlinearity via piecewise linear spline knots or a quadratic component, yet Memory scores decreased linearly with age. Visit was modeled via an indicator for baseline visit 0, given that there was insufficient evidence that subsequent visits differed from each other, yet there was evidence that subsequent visits had higher Memory scores compared with baseline visit 0. Gender was modeled via an indicator for males, who had lower memory scores than females. There was insufficient evidence to support any interactions. Residuals from each model were then robustly standardized to have median 0 and robust SD=1, where the robust SD=IQR/1.35, as 1.35 is the IQR (Inter-Quartile Range) of a standard normal distribution. The choice to use robust measures of location (median) and dispersion (IQR) was made to reduce the influence that cognitively impaired participants might have on the mean and SD, and in recognition of the slight negative skewness of the residuals. The robustly standardized residuals were then viewed as age-gender-education-visit-adjusted robust Z-scores for each of the five cognitive domains.

Defining aMCI/AD, Converters, and NC

For each subject, Zmem(last), Zatt(last), Zexe(last), Zlan(last), and Zvis(last) were defined as the age-gender-education-visit-adjusted robust Z-scores for the last available visit for each subject. The aMCI/AD group was defined as those participants whose adjusted Zmem was 1 IQR below the median at their last available visit, i.e., Zmem(last) $\leq -1.35$. Converters were defined as that subset of the MCI/AD group whose adjusted Zmem at baseline visit 0 was no more than 1 IQR below the median, i.e., Zmem(visit=0) $>-1.35$ and Zmem(last) $\leq -1.35$. Participants were classified as NC if they had central scores on all domains at both the first and last visits, i.e., only if they met all of the following six conditions: (i) $-1<$Zmem(last)$<1$, (ii) $-1<$Zmem(visit=0)$<1$, (iii) Zmin(last) $>-1.35$, (iv) Zmin(visit=0) $>-1.35$, (v) Zmax(last)$<1.35$, and (vi) Zmax(visit=0)$<1.35$, where Zmax(last) and Zmax(visit=0) denote the maximum of the five adjusted Z-scores at the last and first visits, respectively. Zmem for normal participants had to be within 0.74 IQR (1 SD) of the median, rather than just 1 IQR (1.35 SD), to guarantee that they were >0.25 IQR (0.35 SD) from aMCI/AD participants.

Frequency Matching aMCI/AD and NC on Age, Education, and Sex

Comparing the distributions of age, education, and sex for participants classified as aMCI/AD and NC it was observed that NC participants were younger. Given this, and given budget limitations for genetic profiling, NC participants were frequency matched to the aMCI/AD participants for each of the Discovery and Validation samples based on age, education, and sex. This was accomplished by stratifying the sample by four groups of age at the last visit (75-79, 80-85, 86-94, 95-100), three education groups (5-12, 13-18, 19-23), and two sexes (male, female), resulting in 24 age-education-sex strata. An equal number of NC participants were randomly selected to match the aMCI/AD participants per the strata for the Discovery sample, and because one of the strata did not contain a sufficient number of NC participants, the Validation sample had one less NC subject than the a MCI/AD group.

Derivation of the Preclinical Alzheimer's Disease Index (PADI)

For the development of the preclinical Alzheimer's disease Index (PADI), only cognitively normal participants were included at entry (+0.7 SD from the group mean on all domain z-scores) who subsequently either phenoconverted to amnestic MCI or LOAD (Converters, n=28) or remained cognitively normal (NC, n=73) over the course of the study. Time to phenoconversion averaged 2.1 years. The baseline characteristics of the Converter and NC groups were similar except in three cognitive domains: attention, executive function, and memory (Table 6). Stepwise logistic regression revealed that only the attention (OR=0.247, 95% CI: 0.09-0.68) and memory (OR=0.232, 95% CI: 0.10-0.54) z-scores were significant predictors of group. The PADI was constructed by combining the two domains (weighted -0.484 for attention and -0.516 for memory) such that higher scores indicate poorer cognitive performance.

Figure 2:
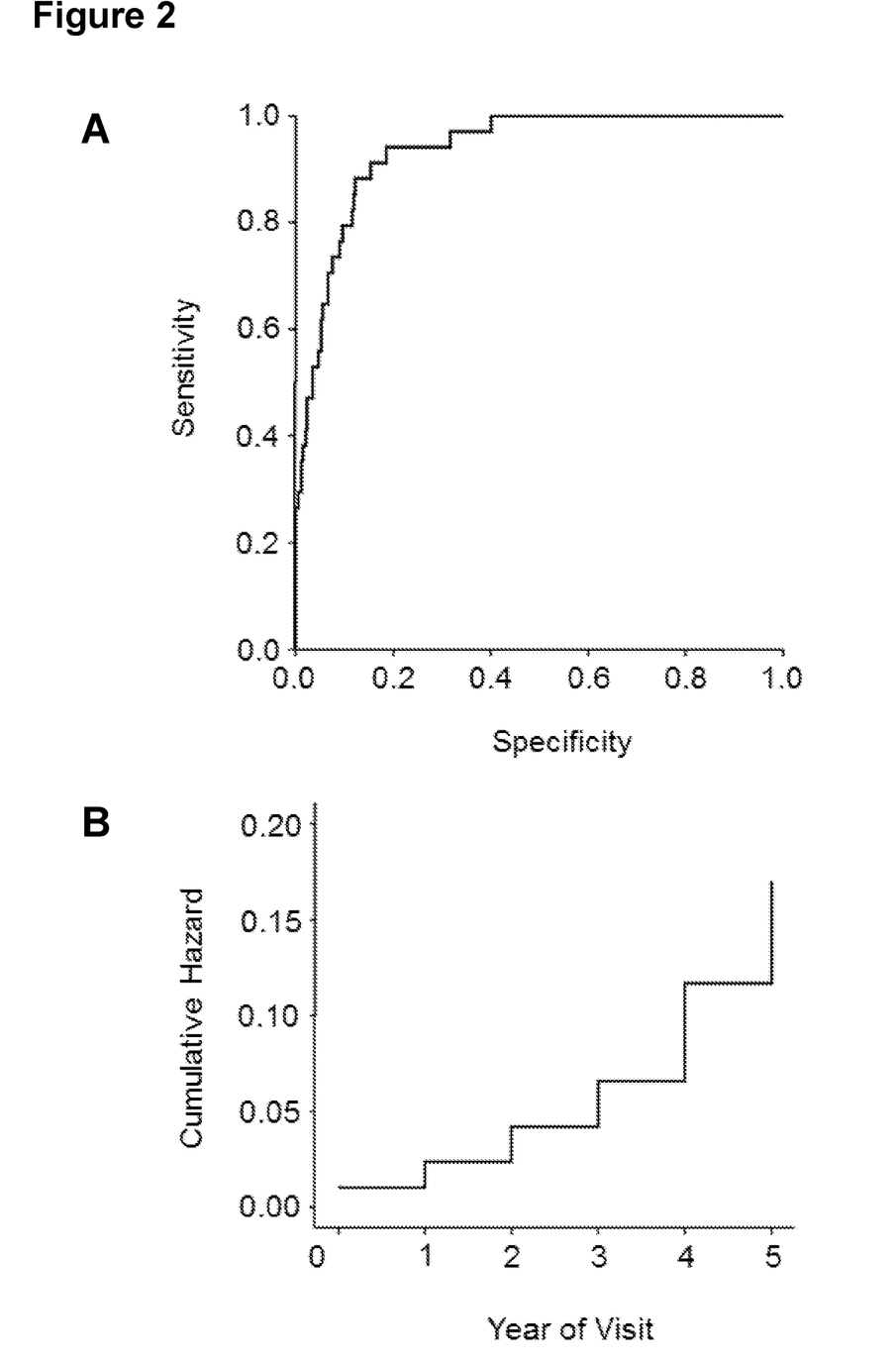
FIG. 2 depicts the performance of the Preclinical Alzheimer's Disease Index (PADI).

The utility of the PADI was tested in the remaining study participants (n=515), to identify phenoconversion risk in subjects not impaired at baseline, but who exhibited subtle deficits that did not allow their consideration as "normal". A total of 35 of the latter met criteria for MCI or AD an average of 1.9 years later. The baseline PADI distinguished these at risk individuals from the rest (ROC AUC=0.93, 95% CI: 0.90, 0.97). Survival analysis, controlling for age, years of education, APOE4 status, global cognition, depression, and subjective memory complaints was also significant (HR=4.57, 95% CI=3.47, 6.01) (FIG. 2).

TABLE 6

Cognitive Measures: Means and Standard Deviations

| Clinical/Cognitive Measures | Dependent Measure (Range) | Domain Assessed | Normal Control (n = 73) | Converter$_{pre}$ (n = 28) | aMCI/AD (n = 74) |
|---|---|---|---|---|---|
| Multiple Assessment Inventory IADL Scale (MAI-IADL) Lawton M P. (1988) Instrumental Activities of Daily Living (IADL) scale: Original observer-rated version. Psychopharmacology Bulletin, 24, 785-7. | Total Score (0-27) | Functional capacities | 26.51 (1.71) | 26.65 (0.87) | 24.82 (3.60) |
| Multifactorial Memory Questionnaire (MMQ) Troyer A K and Rich J B. (2002). Psychometric properties of a new metamemory questionnaire for older adults. Journal of Gerontology, 57(1), 19-27. | Total Score (0-228) | Memory complaints | 130.32 (19.93) | 139.71 (13.36) | 121.01 (18.14) |
| Mini Mental State Examination (MMSE) Folstein, M F, Folstein, S E, and McHugh, P R. (1975). "Mini-mental state". Journal of Psychiatric Research, 12, 189-98. | Total Score (0-30) | Global cognitive ability | 28.64 (1.30) | 28.61 (2.49) | 26.32 (2.87) |
| Geriatric Depression Scale-Short Form (GDS-SF) Sheikh J I and Yesavage J A. (1986). Geriatric Depression Scale (GDS): Recent evidence and development of a shorter version. Clinical Gerontologist, 5, 165-173. | Total Score (0-15) | Mood | 1.47 (2.02) | 1.32 (2.28) | 1.97 (2.7) |
| Wechsler Memory Scale-III Forward Digit Span (WMS-III FDS) Wechsler D. Wechsler Memory Scale-III Manual. San Antonio, TX: The Psychological Corporation, 1997. | Span Length (0-9) | Attention | 6.25 (1.05) | 6.18 (0.95) | 6.14 (1.13) |
| Trail Making Test-Part A (TMT-A) Reitan R M. (1958). Validity of the Trail Making Test as an indicator of organic brain damage. Perceptual and Motor Skills, 8, 271-6. | Completion time (1-300 sec) | Attention | 36.69 (13.23) | 46.14 (14.75) | 55.26 (44.63) |
| Wechsler Memory Scale-III Backward Digit Span (WMS-III BDS) Wechsler D. Wechsler Memory Scale-III Manual. San Antonio, TX: The Psychological Corporation, 1997. | Span Length (0-8) | Executive ability | 4.34 (0.9) | 4.29 (0.76) | 4.01 (0.91) |
| Trail Making Test-Part B (TMT-B) Reitan R M. (1958). Validity of the Trail Making Test as an indicator of organic brain damage. Perceptual and Motor Skills, 8, 271-6. | Completion Time (1-300 sec) | Executive ability | 98.53 (41.30) | 134.57 (63.89) | 151.99 (69.82) |
| Category fluency (Animals) Borkowski J, Benton A, Spreen O. (1967). Word fluency and brain damage. Neuropsychologia, 5, 135-140 | Animals named in 1-minute | Language | 20.91 (4.72) | 19.0 (5.24) | 15.16 (5.03) |
| Boston Naming Test 60-Item version (BNT-60) Kaplan E, Goodglass H, and Weintraub S. (1983). Boston Naming Test. Philadelphia: Lea & Feibiger. | Total Correct (0-60) | Language | 56.29 (3.19) | 53.14 (7.96) | 50.51 (9.46) |
| Rey Auditory Verbal Learning Test Learning (RAVLT Learning) Rey A. (1964). L'examen clinique en psychologie. Paris: Presses Universitaires de France. | Total words recalled over Trials 1-5 (0-75) | Verbal learning | 43.43 (7.76) | 37.0 (5.88) | 27.08 (7.01) |
| Rey Auditory Verbal Learning Test Recall (RAVLT Retrieval) Rey A. (1964). L'examen clinique en psychologie. Paris: Presses Universitaires de France. | Words recalled at 20-minute delay (0-15) | Verbal retrieval | 7.84 (2.48) | 5.32 (2.59) | 1.93 (1.64) |
| Rey Auditory Verbal Learning Test Retention (RAVLT Recognition) Rey A. (1964). L'examen clinique en psychologie. Paris: Presses Universitaires de France. | True pos.-false pos. (0-15) | Verbal retention | 13.30 (1.57) | 11.14 (2.24) | 7.09 (3.15) |
| Hooper Visual Organization Test (HVOT) Hooper H E. Hooper Visual Organization Test (VOT) Los Angeles: Western Psychological Services; 1983. | Total score (0-30) | Visuo-perception | 23.96 (3.05) | 22.36 (3.72) | 20.93 (4.51) |

TABLE 7

PADI Baseline Demographic and Health Characteristics.

| | NC (n = 73) | Converter (n = 28) | t or $\chi^2$ value, df (p) |
|---|---|---|---|
| Age, M (SD) | 80.03 (3.63) | 79.86 (4.21) | 0.18, 89 (.86) |
| Male, n (%) | 27 (39.1%) | 10 (45.5%) | 0.28, 1 (.60) |
| Years of education, M (SD) | 15.52 (2.37) | 15.18 (2.84) | 0.56, 89 (.58) |
| APOE4 carrier, n (%) | 16 (23.2%) | 4 (18.2%) | 0.24, 1 (.62) |
| Depression, M (SD) | 1.28 (1.99) | 1.41 (2.50) | −0.26, 89 (.80) |
| Memory complaints, M (SD) | 26.61 (0.79) | 26.59 (0.96) | 0.09, 89 (.93) |
| Global cognition, M (SD) | 28.86 (1.18) | 28.68 (2.68) | 0.43, 89 (.67) |
| Attention, M (SD) | 0.03 (0.51) | −0.36 (0.59) | 3.24, 94 (.002) |
| Executive function, M (SD) | −0.08 (0.56) | −0.49 (0.89) | 2.31, 35 (.027) |
| Language, M (SD) | 0.11 (0.52) | −0.22 (1.01) | 1.61, 30 (.12) |
| Memory, M (SD) | 0.11 (0.65) | −0.40 (0.75) | 3.41, 99 (.001) |
| Visuoperception, M (SD) | 0.22 (0.68) | −0.10 (1.04) | 1.50, 37 (.14) |

Note.
Depression was measured using 15-item Geriatric Depression Scale; Memory complaints were measured using the Multifactorial Memory Questionnaire; Global cognition was measured using Mini Mental State Examination.

What is claimed is:

1. A method of treating memory impairment in a subject in need thereof, the method comprising
    (a) determining whether the subject has an increased risk of suffering from memory impairment by obtaining the influx of at least one polyunsaturated fatty acid (PUFA) from plasma into the brain of the subject, and comparing the subject's measured influx with a normal influx to determine if the subject's flux is increased compared to a normal influx, wherein an increase in the subject's influx over normal influx is indicative that the subject has an increased risk of suffering from memory impairment compared to a normal individual; and (b) administering a treatment for memory impairment to the subject when the subject is determined to have an increased risk of memory impairment.

2. The method of claim 1, wherein the at least one PUFA is a labeled PUFA that is administered to the subject.

3. The method of claim 1, wherein the at least one PUFA is selected from the group consisting of omega-3 fatty acids and omega-6 fatty acids.

4. The method of claim 3, wherein the at least one PUFA is an essential PUFA.

5. The method of claim 4, wherein the essential PUFA is selected from the group consisting of linoleic acid (LA) and alpha linolenic acid (ALA).

6. The method of claim 1, wherein the methods measure the influx of two, three or four PUFAs.

7. The method of claim 6, wherein the PUFAs are labeled PUFAs that are administered to the subject.

8. The method of claim 7, wherein the labeled PUFAs are linoleic acid (LA) and alpha linolenic acid (ALA).

9. The method of claim 1, wherein the normal influx comprises the subject's influx prior to the onset of memory impairment.

10. The method of claim 1, wherein the normal influx comprises the subject's influx (i) when the subject is deemed to possess normal cognitive abilities, (ii) when the subject has no signs of memory impairment, or (iii) a combination thereof.

11. The method of claim 1, wherein the normal influx comprises an influx profile generated from an individual or group of individuals that are assessed to have normal memory ability.

12. The method of claim 1, wherein the normal influx comprises an influx profile generated from an individual or group of individuals who display no memory impairment.

13. The method of claim 1, wherein the determination of whether the subject has an increased risk of suffering from memory impairment further comprises assessing the subject's Preclinical Alzheimer's Disease Index (PADI).

14. The method of claim 1, wherein the treatment is selected from the group consisting of fenofibrate; cholinesterase inhibitor; memantine, a mixture of one or more of omega-3 fatty acids, choline, uridine monophosphate and a mixture of antioxidants and B vitamins; coconut oil; ginger; green tea; fatty fish; cold-water fish; soy products; dark berries; green leafy vegetables; cruciferous vegetables; and a combination thereof.

* * * * *